United States Patent
Gulyamov

(10) Patent No.: US 10,570,466 B2
(45) Date of Patent: *Feb. 25, 2020

(54) METHOD FOR EVALUATION OF VIABILITY OF VIRUSES WITH LYMPHOTROPISM PROPERTIES

(71) Applicant: Ovik Leonardovich Mkrtchyan, Tashkent (UZ)

(72) Inventor: Nariman Gulyamov, Tashkent (UZ)

(73) Assignee: Ovik Leonardovich Mkrtchyan, Tashkent (UZ)

(*) Notice: Subject to any disclaimer, the term of this patent is extended or adjusted under 35 U.S.C. 154(b) by 0 days.

This patent is subject to a terminal disclaimer.

(21) Appl. No.: 15/966,513

(22) Filed: Apr. 30, 2018

(65) Prior Publication Data

US 2018/0245167 A1    Aug. 30, 2018

Related U.S. Application Data

(60) Continuation of application No. 15/257,663, filed on Sep. 6, 2016, now Pat. No. 9,957,579, which is a division of application No. 14/397,680, filed as application No. PCT/UZ2013/000001 on May 21, 2013, now Pat. No. 9,879,329.

(30) Foreign Application Priority Data

Jun. 18, 2012  (UZ) .................................... 20120233

(51) Int. Cl.
*C12Q 1/70*    (2006.01)
*C12Q 1/6806*  (2018.01)

(52) U.S. Cl.
CPC ........... *C12Q 1/703* (2013.01); *C12Q 1/6806* (2013.01); *C12Q 1/70* (2013.01); *C12Q 1/706* (2013.01); *C12Q 1/707* (2013.01)

(58) Field of Classification Search
None
See application file for complete search history.

(56) References Cited

U.S. PATENT DOCUMENTS

| | | | | |
|---|---|---|---|---|
| 5,674,680 A | * | 10/1997 | Saksela | C12Q 1/703 435/5 |
| 9,873,922 B2 | * | 1/2018 | Gulyamov | C12Q 1/70 |
| 9,957,579 B2 | * | 5/2018 | Gulyamov | C12Q 1/703 |
| 2009/0176202 A1 | | 7/2009 | Jenkins et al. | |

OTHER PUBLICATIONS

Naslund et al. (Journal of Virological Methods, 2011, vol. 178, p. 186-190).*
Cochrane et al. (Journal of Virology, 2004, vol. 78, p. 9862-9871).*
ISR and Written Opinion, for PCT/UZ2013/00001.
Examination Report, for 10904/DELNP/2014, Indian Patent Office.
First and Second Office Action, for 201380006383.7, China Patent Office.
Search Reports, for 13 807 284.8-1404, European Patent Office.
Koya Ariyoshi et al., "Development of a Rapid Quantitative Assay for HIV-1 Plasma Infectious Viraemia-Culture-PCT (CPID)," J. of Mdeical Virology 43:28-32 (1994).
C. Bagutti et al.,"Detection of adeno- and lentiviral (HIV1) contaminations on lab. surfaces as a tool for the sury of biosafety standards," J. of Applied Micro(2011) 70-82.
Charles Bangham, "The Immune control and cell-to-cell spread of human T-lymphotropic virus type 1," J. of General Virology (2003), 84, 3177-3189.
J. Black et al., "Frequent isolation of human herpesvirus 7 from saliva," Virus Research, 29 (1993) 91-98.
M. Cabrerizo et al., "In vitro infection of human peripheral blood . . . viral genome," J. of Viral Hepatitis, 2002, 9, 265-271.
Akiko Ishii-Watabe et al., "detection of Replication-Competent Adenoviruses . . . PCR," Molecular Therapy, vol. 8, No. 6, Dec. 2003, 1009-1016.

* cited by examiner

*Primary Examiner* — Agnieszka Boesen
(74) *Attorney, Agent, or Firm* — Van Dyke IP Law; Raymond Van Dyke

(57) ABSTRACT

Methods and techniques to increase the reliability of detecting virus infections, particularly lymphotropism, to eliminate false negative reactions in testing blood for the presence of lymphotropic viruses during enzyme immunoassay (EIA) and polymerase chain reaction (PCR) testing, and to better detect viruses with lymphotropism in biological materials having a concentration of virus particles lower than the sensitivity threshold of existing EIA and PCR methods, thereby making the techniques of the present invention more reliable.

20 Claims, No Drawings

METHOD FOR EVALUATION OF VIABILITY OF VIRUSES WITH LYMPHOTROPISM PROPERTIES

CROSS REFERENCE TO RELATED PATENT APPLICATIONS

The present invention is a continuation of U.S. patent application Ser. No. 15/257,663, filed Sep. 6, 2016, now U.S. Pat. No. 9,957,579, entitled "METHOD FOR EVALUATION OF VIABILITY OF VIRUSES WITH LYMPHOTROPISM PROPERTIES," which is a divisional of U.S. patent application Ser. No. 14/397,680, filed Oct. 29, 2014, now U.S. Pat. No. 9,879,329, also entitled "METHOD FOR EVALUATION OF VIABILITY OF VIRUSES WITH LYMPHOTROPISM PROPERTIES," which is a United States nationalization of PCT/UZ2013/000001, filed May 21, 2013, and claims priority from Uzbekistanian Patent Application No. IAP 2012 0233, filed Jun. 18, 2012, entitled "METHOD FOR EVALUATION OF VIABILITY OF VIRUSES WITH LYMPHOTROPISM PROPERTIES," the subject matters of which are incorporated by reference herein in their entirety.

TECHNICAL FIELD

The present invention relates to methods of detection of viruses with lymphotropism properties in biological substrates with low concentration of viral particles, evaluation of their viability and elimination of false-negative results of enzyme immunoassay (EIA) and polymerase chain reaction (PCR) testing, and techniques related thereto that may be used in the medical industry and biotechnology.

BACKGROUND OF THE INVENTION

The detection of viruses in biological substrates through isolation in cell cultures is a well-known technique. As is known, viruses isolated by cell culture methods are identified by haemadsorption, hemagglutination or indirect immunofluorescence methods. Proper sampling and short-time transportation to the laboratory venue on appropriate media are essential for effective isolation of viruses isolated in culture, which preserves virus viability and restricts bacteria and fungi reproduction. Many viruses, in particular the hepatitis B virus (HBV), the hepatitis C virus (HCV) and the human immunodeficiency virus (HIV), are anthroponotic viruses, i.e., affecting human cells only and thus causing diseases only to humans.

It should be understood that there are no experimental models of these infections. Also, there are no cultivated cell cultures, particularly in the Republic of Uzbekistan, on which one may adequately study cytopathogenic properties and viability of these viruses in vitro. Moreover, because of the complexity, the isolation of viruses on cell cultures is not generally used for diagnostic purposes.

An immunological method for the detection of viruses in biological material is known as an enzyme-linked, immunosorbent assay (ELISA), which is based on the use of specific viral proteins extracted from infected cells or produced by genetic engineering, e.g., by the detection and comparison of antibodies to the number of virus antigens.

In some virus infections, e.g., HCV, enzyme immunoassay (EIA) detects the antibodies only, thus substantially restricting evaluation of the progress and activity of an infection. Moreover, EIA, in operation, has sensitivity threshold values, below which the detection of viruses becomes impossible.

With regard to methods of detection of viruses with lymphotropism properties in the biological materials, virus viability assessment, and the exclusion of false-negative results of EIA and PCR, the closest analog is the detection of viral RNA or DNA by the sampling of biological material and the detection of the presence of viral RNA or DNA by polymerase chain reaction (PCR).

The method and techniques of the instant invention relate to direct methods for the detection of the pathogen in biological materials, thereby permitting the evaluation of the activity of viral processes, where a positive PCR-reaction confirms the presence of the virus in the liver and in the blood with a high probability. However, PCRs of the biological samples (plasma or blood proteins, tissue or organ biopsy materials) do not always allow the detection of infections caused by viruses with lymphotropism properties, though such viruses may persist in substantially high concentrations in the lymphoid tissue (false-negative results of PCR), and vice versa a positive PCR may be obtained without persistence of viruses. Furthermore, PCR has a sensitivity threshold, below which virus presence is not detectable by this method, yet another drawback in the prior art. These and other drawbacks in the prior art lead to unreliable testing and detection of viruses, particularly viruses with lymphotropism properties.

There is, therefore, a present need for an improved technique for the reliable detection of viruses, particularly those viruses with lymphotropism properties.

There is also a need for new techniques for the elimination of the aforementioned false-negative results when testing blood for these viruses, particularly the elimination of false-negative results testing blood for the presence of lymphotropic viruses by EIA and PCR.

There is a further need for new techniques that can better detect viruses with lymphotropism properties in the biological materials where virus concentrations are low, for example, below the threshold of current IFA or PCR methods sensitivities.

These and many other objects are met in various embodiments of the present invention, offering significant advantages over the known prior art and consequent benefits to all mankind. The objects and features of the present invention, will become apparent in the detailed description of the invention set forth below.

SUMMARY OF THE INVENTION

The present invention is directed to methods and techniques to increase the reliability of detecting virus infections, particularly lymphotropism, to eliminate false negative reactions in testing blood for the presence of lymphotropic viruses during enzyme immunoassay (EIA) and polymerase chain reaction (PCR) testing, and to detect viruses with lymphotropism in biological material having a concentration of virus particles lower than the sensitivity threshold of existing EIA and PCR methods, thereby making the techniques of the present invention more reliable.

The methods and techniques of the present invention assess the viability of viruses with lymphotropism by collecting biological material and determining whether said material contains virus RNA or DNA, e.g., by conducting a polymerase chain reaction (PCR reaction). In addition, a lymphocyte suspension is taken from the blood of healthy people, to which lymphocytes an equal volume of biological material is added. This combination is then mixed, preferably incubated at a temperature of about 37° C. for a period of about 6-8 hours, and the lymphocytes are washed of plasma and broken down. The lymphocyte cytoplasm is then subjected to PCR testing. The detection of virus RNA or DNA in the lymphocyte cytoplasm indicates that the viruses have retained their viability. Correspondingly, the absence of virus RNA or DNA in the lymphocyte cytoplasm indicates the inactivation of the viruses. In this manner the method and technique of the present invention allows assessment of the viability of a variety of viruses, including the HBV, HCV and HIV viruses.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The principles of the present invention are achieved through the evaluation of the viability of the viruses with lymphotropism properties by sampling of the biological material, detection of presence of viral RNA or DNA using the polymerase chain reaction (PCR), as briefly discussed hereinabove. As described, a lymphocytes suspension is obtained from healthy human blood and an equal amount of biological material is then added. The aforesaid admixture is stirred, and then incubated at about 37° C. for about 6-8 hours, resulting in the washing-out of the lymphocytes from the plasma, and the lymphocytes being destroyed. The lymphocytes' cytoplasm is then subjected to a PCR test.

As discussed, the detection of viral RNA or DNA in the cytoplasm of lymphocytes indicates the preserved viability of viruses, whereas the absence of viral RNA or DNA viruses in the cytoplasm of lymphocytes indicates inactivation of viruses. It should be understood that plasma or blood serums, biopsy samples of tissue or organs, and the washouts from the medical instruments may be used as the biological samples. In this manner, the methodologies and techniques of the instant invention allow assessment of the viability of viruses, particularly the HBV, HCV and HIV viruses.

As discussed, another objective of the present invention is the elimination of EIA and PCR false-negative results, such as by obtaining blood from patients suspected of being infected by lymphotropic viruses. For this approach, about 6-8 ml of such blood is drawn into test tubes, which preferably contain about 2.0 ml normal saline and about 2-3 drops of heparin. The lymphocytes are then separated from the blood and incubated at about 37° C. for about 6-8 hours, where lymphocytes are washed-out from the plasma and destroyed, and the cytoplasms of lymphocytes are then subjected to PCR. As discussed hereinabove, the detection of viral RNA or DNA in the lymphocytes' cytoplasm indicates the presence of viruses, whereas the absence of viral RNA or DNA in the lymphocytes' cytoplasm indicates the absence of viruses in the blood. The content of a patient's lymphocyte is thus subjected to PCR-testing.

It is known that many viruses, particularly those of the aforementioned hepatitis B virus (HBV), hepatitis C virus (HCV) and human immunodeficiency virus (HIV) can replicate in mononuclear blood cells, particularly, in the lymphocytes and in macrophages. It is known that HBV- and HCV-infections simultaneously cause inflammatory processes in the liver with subsequent hepatitis, as well as secondary immunodeficiency with various degrees of T-lymphopenia and B-lymphopenia, imbalance of regulatory subpopulations of T-lymphocytes (T-helpers and T-suppressors), reduction of immune regulatory index (IRI), and dysgammaglobulinemia. The degree and grade of immunodeficiency, however, has been found to have no relation to the degree of the pathologic process in the liver. Indeed, patients with chronic HBV and HCV infections have different intensities of pathological processes in the liver tissue after some time, from weak to expressed, but nonetheless have stable and steady aggravation of secondary immunodeficiencies.

The dissociation of the degree of liver tissue injury and the degree of secondary immunodeficiency in various nosological forms of chronic virus hepatitis supports the idea that the hepatitis and secondary immunodeficiency in HBV and HCV infections are associated, mutually aggravating, but not mutually conditional. In other words, HBV and HCV, along with hepatotropic property viruses, possess expressed lymphotropic properties—direct properties that cause secondary immunodeficiencies. The differences in clinical appearances of the liver tissue injuries and the degree of immunodeficiency in HBV and HCV infections are due to differences in the degree of hepatotropic and lymphotropic properties of these viruses. Thus, the differences in the degrees of hepatotropic and lymphotropic properties of viruses determine the differences of the pathogenesis, clinical appearance and the pattern of antiviral therapy effects in chronic HBV and HCV infections in various stages of these diseases.

The identity of the lymphotropic properties of the aforesaid HBV and HCV, and HIV viruses, besides secondary immunodeficiency forming, is confirmed also by commonality of their epidemiological features, mechanism of transfer, progress of associated opportunistic infections (frequent respiratory diseases, intestinal infections), and particularly the development of the lymphogranulomatosis in different tissues of the organism. The development of lymphoid follicles' clusters, which is the aforementioned lymphogranulomatosis, in various organs and tissues of the organism is considered intrinsic for viral infections of the lymphoid cell system.

When considering the lymphotropic properties of HBV, it was found that regardless of the serum titer, HBV can permanently persist in high concentrations in the cytoplasm of lymphoid elements. This phenomenon is used in the context of the instant invention for reliable increasing and elimination of the aforesaid false-negative results by EIA and PCR, and the detection of lymphotropic viruses in biological material with concentrations of viral particles below the threshold of test-sensitivity for the EIA and PCR techniques, as generally described hereinabove.

In the instant invention, Applicant employed the lymphotropic properties of HBV, HCV and HIV in an evaluation method of virus viability—the ability of these viruses to penetrate and persist intracellularly in the healthy human lymphocytes during their in vitro incubation.

It should be understood that the evaluation of the viability of viruses with lymphotropism properties, particularly HBV, HCV and HIV, required the long-term storage of viruses, and the control of the antiviral efficiency of various disinfecting chemicals and physical factors against these viruses, as well as the control of antiviral therapy, as described in more detail hereinbelow.

Below is a description of a method pursuant to the teachings of an embodiment of the present invention directed to the evaluation of the viability of viruses with lymphotropism properties.

I. Producing a Suspension of Viruses with Lymphotropism Properties

In the production of a suspension of viruses, the biological material (plasma or blood serum, biopsy samples of tissue or organs, and/or the wash-outs from medical instruments) is obtained. Then the biological material is subjected to quantitative PCR for the verification of the presence of viruses with lymphotropism properties, and the quantification of titer of the viruses. Viruses contained in the biological material are kept in a frozen state in a refrigerator at below about −25° C. temperature.

II. Producing a Lymphocytes Suspension from a Healthy Human Subject a) healthy volunteers are tested for infection with lymphotropic viruses using EIA, as described. Lymphocytes from healthy people with a negative result for study viruses are used in the investigations;

b) to receive a sufficient amount of lymphocyte, blood is taken from an ulnar vein in an amount of about 20-30 ml in the morning from a fasting, healthy human subject. Then about 7-8 ml of the blood is transferred to respective centrifuge tubes containing about 2 ml normal saline and about 3 drops of heparin ("Heparin" concentration of 5000 ME/ml; 3 drops contain 750 ME/ml of heparin). The resulting solution is then stirred thoroughly;

c) the lymphocytes are separated from the whole heparin containing blood in a ficoll-verografin gradient with density d=1.077 g/ml pursuant to a technique known in the art. Then, about 2 ml of the aforesaid ficoll-verografin gradient is poured into a clean centrifuge tube, then the heparinized blood lays on its surface and the tube is centrifuged at about 1500 RPM for about 20 minutes. During centrifugation, all blood cells, excluding lymphocytes, penetrate through the aforesaid ficoll-verografin gradient. Blood plasma, however, remains above the gradient. In the border of the ficoll-verografin gradient and the plasma, there is a peculiar turbid ring, consisting of pure lymphocytes so formed. The ring with lymphocytes is then carefully pumped with a pipette and transferred to a clean centrifugal tube;

d) the lymphocytes are then washed-out with about 10 ml of normal saline 2-3 times with further centrifugation at about 1500 RPM for about 20 minutes; and e) after the last centrifugation in the previous step, the supernatant is removed. The sediment containing lymphocytes is diluted and re-suspended in about 600 µl of normal saline. It should be understood that a lymphocytes suspension so produced may be stored no more than about a day at a temperature of about +4° C.

III. Evaluation of Viruses with Lymphotropism Properties to Penetrate and Persist Intracellularly in the Human Lymphocytes In Vitro 1) Biological material containing viruses with lymphotropism properties is taken from a refrigerator and thawed at room temperature;

2) an equal amount (about 300 µl) of virus-containing biological material and a suspension of healthy human lymphocytes is transferred with a pipette to a clean centrifugal tube, and the contents are mixed and placed for incubation (incubation of viruses with lymphocytes in vitro) into a thermostat at about +37° C. for about 6-8 hours. The testing tube is preferably mixed with shacking every 1.5-2 hours;

3) The washing-out of lymphocytes is then done. The aforesaid testing tube is removed from the thermostat. About 6-8 ml of normal saline is added, mixed and the admixture centrifuged at about 1500 RPM for about 20 minutes. The lymphocytes are then sediment at the bottom of the tube. The supernatant (mixture of plasma with saline) is then entirely removed. The lymphocytes are washed out in normal saline and sediment 2-3 times. After the last centrifugation and supernatant removal, the suspension of the lymphocytes (sediment) is diluted with about 500 µl of normal saline and transferred to a plastic 1.5 lock tube (Eppendorf tube) or similar tube;

4) Thereafter, the tube is placed into a freezer, such as a house grade refrigerator, overnight. The lymphocytes are thereby destroyed under these slow freezing conditions;

5) The removal of the membrane of destroyed lymphocytes. The next day the tubes from the freezer are thawed at room temperature. Then the membranes of the aforesaid destroyed lymphocytes are removed by centrifugation at about 3000 RPM for about 30 minutes. Membranes are precipitated on the bottom of the tube and the lymphocytes' cytoplasm content remains in the supernatant; and 6) The supernatant from the tube is transferred and subjected to quantitative PCR for testing for possible viral RNA or DNA in the cytoplasm of the lymphocytes that were previously in the infected patient's plasma.

IV. Assessment of the Results

1. Positive PCR for the presence of viral RNA or DNA in the cytoplasm of lymphocytes indicates the remaining virus viability, i.e., the virus' ability to penetrate and persist in human lymphocytes in vitro.

2. Negative PCR for the presence of viral RNA or DNA in the cytoplasm of lymphocytes indicates the loss (inactivation) of virus viability, i.e., the loss of the virus' ability to penetrate and persist in human lymphocytes in vitro.

The following examples further support the presently-claimed invention:

Example #1: The Assessment of Viability of Viruses with Lymphotropism Properties The blood is obtained from an ulnar vein of a patient after receiving antiviral therapy for hepatitis C. The plasma is then separated from whole blood and subjected to quantitative PCR for the verification of the presence of HCV and quantification virus titer. In this embodiment, the PCR testing is negative. Tested plasma is kept in the freezer at below −25° C. temperature.

Simultaneously a 20-30 ml sample of blood from healthy human volunteers is obtained in the morning from an ulnar vein. The blood plasma portion is then subjected to PCR analysis for viruses with lymphotropism properties infection. The lymphocytes from the healthy humans, with negative testing results for infection, are used for further investigation. Then 7-8 ml blood aliquots are transferred to centrifuge tubes containing about 2 ml of normal saline and about 3 heparin drops ("Heparin" concentration is 5000 ME/ml, 3 drops contain 750 ME/ml of heparin). The solution in the tube is then mixed thoroughly. As described hereinabove, the lymphocytes are separated from the whole heparinized blood in a ficoll-verografin gradient with d=1.077 g/ml density according to a known method by Garib, Yu et al. Then, about 2 ml of the aforesaid ficoll-verografin gradient is poured into a clean centrifuge tube, where heparinized blood lays on the surface of the gradient and then is centrifuged at about 1500 RPM for about 20 minutes.

All blood cells, excluding lymphocytes, penetrate the ficoll-verografin gradient and the sediment underneath. The blood plasma is found above the aforesaid gradient. Along the border between the ficoll-verografin gradient and the plasma, the afore-noted peculiar turbid ring with pure lymphocytes suspension is formed. The ring with lymphocytes is then carefully sucked up with a pipette, and transferred to a clean centrifuge tube. The lymphocytes are washed out in normal saline and sedimented about 2-3 times. After the last centrifugation, the supernatant is removed. The sediment containing lymphocytes is then diluted with about 600 µl saline and re-suspended. As is understood, the lymphocytes suspension so formed may be stored for about 1 day at about +4° C. temperature.

The testing plasma from the freezer is then thawed at room temperature. Equal volumes (about 300 µl) of plasma and the suspension of lymphocytes are transferred to a clean centrifuge tube with a pipette, mixed and placed for incubation in a thermostat at about +37° C. temperature for about 6-8 hours. The tube is then mixed by shaking every about 1.5-2 hours.

After incubation, the tube is removed from the thermostat. Then, about 6-8 ml of saline is added, mixed and centrifuged at about 1500 RPM for about 20 minutes. As discussed, the lymphocytes sediment at the bottom of the tube. The supernatant (mixture of plasma and normal saline) is then removed. With 2-3 times wash-out in normal saline and the lymphocytes sedimentation is performed in the same fashion. After the last centrifugation, the supernatant is removed, and a suspension of lymphocytes (sediment) is diluted by adding about 300 µl of normal saline, and transferred to a 1.5 ml lock tube, such as an Eppendorf tube.

Thereafter, lymphocyte membranes are destroyed by placing them overnight in a house-grade freezer. On the next day, the tubes are thawed at room temperature. Then, the membranes of the destroyed lymphocytes are removed from the suspension by centrifugation of the tube at about 3000 RPM for about 30 minutes. The membranes are thereby precipitated at the bottom of the tubes, and the lymphocyte cytoplasm contents remain in the supernatant, as also described hereinabove. The supernatant is then transferred from the tube and subjected to a quantitative PCR test for the presence of HCV viruses in the cytoplasm of the lymphocytes. A positive PCR test for HCV, of course, indicates the preservation of the HCM viability and the requirement of further antiviral therapy.

Example #2

A liver tissue, such as sampled by a liver puncture of a patient, who was given antiviral therapy for hepatitis B is obtained. A liver biopsy sample thereof is homogenized in an about 1.5 ml normal saline; transferred to a centrifuge tube, and then centrifuged at about 1500 RPM for about 20 minutes; and the supernatant transferred to a tube. One part of the supernatant is then subjected to quantitative PCR testing for the presence of HCV virus and quantification of virus titer. If the PCR test for HCV is positive, the biopsy sample is kept in the freezer in the refrigerator at below −25° C. temperature.

A lymphocyte suspension from a healthy human is made, as described hereinabove in connection with Example #1.

The supernatant from the aforesaid liver biopsy sample homogenate is thawed at room temperature. Then equal volumes (about 300 µl) of the supernatant and lymphocyte suspension are added to a tube by an automatic pipette or similar such means; the resulting solution is admixed and placed for incubation into a thermostat at about +37° C. temperature for about 6-8 hours, where the testing tube is mixed by shaking about every 1.5-2 hours.

The tube is the removed from thermostat and about 6-8 ml of normal saline is added, admixed and centrifuged at about 1500 RPM for about 20 minutes. The lymphocytes sediment at the bottom of the tube, as described hereinabove. The supernatant (mixture of plasma with normal saline) is removed entirely, and treated by a 2-3 times wash-out in normal saline, where the aforementioned lymphocytes sedimentation is performed in the same fashion as before. After the last centrifugation, the supernatant is removed and the suspension of lymphocytes (in the sediment) is diluted by adding about 300 µl of normal saline. Thereafter, the destruction of the lymphocyte membranes is performed by putting the testing tube into a house-grade freezer overnight.

Accordingly, lymphocyte membranes are destroyed by overnight placement into house-grade freezer. On the next day, the tubes are thawed at room temperature. Then, the membranes of destroyed lymphocytes are removed from suspension by centrifugation of the tube at about 3000 RPM for about 30 minutes. The membranes are precipitated along the bottom of the tubes and the lymphocyte cytoplasm contents remain in the supernatant, as discussed and described hereinabove. The supernatant is transferred from the tube and subjected to a quantitative PCR test for the presence of HBV virus in the cytoplasm of the lymphocytes, where a negative PCR test for HBV indicates the virus' loss of viability (inactivation).

Example #3

This example concerns the detection of viruses with lymphotropism properties in biological material with the concentration of virus below EIA and PCR sensitivity thresholds.

In a blood center, the blood plasma from about 6-8 ml of blood is tested for viruses with lymphotropism properties. One part of the plasma is subjected to quantitative PCR testing for the presence of HBV, HCV or HIV viruses, and the quantification of virus titer, where the PCR test here for the presence of viruses is negative. The tested plasma is stored in a freezer at below about −25° C.

The lymphocyte suspension from healthy human subjects is then prepared as described in more detail hereinabove in connection with Example #1.

The testing plasma from the freezer is thawed at room temperature. Equal volumes (about 300 µl) of plasma and the suspension of lymphocytes is transferred to a clean centrifuge tube using an automatic pipette, admixed and placed for incubation in a thermostat at about +37° C. for about 6-8 hours. The tube is mixed by shaking about every 1.5-2 hours.

The tube is then removed from the thermostat, and about 6-8 ml of normal saline is added, admixed and centrifuged at about 1500 RPM for about 20 minutes. As described hereinabove, the lymphocytes sediment along the bottom of the tube. The supernatant (mixture of plasma with normal saline) is removed entirely, and the remainder 2-3 times wash-out in normal saline, where the lymphocytes sedimentation is performed in the same manner as set forth hereinabove. After the last centrifugation, the supernatant is removed and the suspension of lymphocytes (sediment) is diluted by adding about 300 µl of normal saline.

Thereafter, the lymphocyte membranes are destroyed by placing them into a house-grade freezer overnight. On the next day, the tubes are thawed at room temperature. The membranes of the destroyed lymphocytes are removed from suspension by centrifugation of the tube at about 3000 RPM for about 30 minutes. As discussed, the membranes precipitated along the bottom of the tubes, and the lymphocyte cytoplasm contents remain in the supernatant. The supernatant is then transferred from the tube and subjected to quantitative PCR testing for the detection of HBV, HCV and HIV viruses in the content of lymphocytes' cytoplasm, where a positive PCR for HCV indicates the presence of HCV virus in the donor plasma, indicating that donor's ineligibility for transfusion.

Example #4: The Elimination of EIA and PCR False-Negative Results

In this example, about 6-8 ml of blood is obtained in the morning from a fasting donor, preferably from an ulnar vein. Whole blood is then transferred to a tube, subjected to sedimentation techniques, as described herein, and a serum is obtained; one part of the serum is subjected to a PCR test for the presence of HBV, HCV or HIV viruses. and the quantification of virus titer, where the PCR tests are negative. The rest of the blood serum is stored in the tube. The lymphocyte suspension from a healthy human subject is performed, as described in more detail hereinabove in connection with Example #1.

The lymphocytes are separated and destroyed by overnight freezing in a house-grade refrigerator, as described. On the next day, the tube is thawed at room temperature. Then the membranes of the destroyed lymphocytes are removed from the suspension by centrifugation at about 3000 RPM for about 30 minutes. The membranes precipitate on the bottom of the tube, and lymphocyte cytoplasm contents remain in the supernatant. The supernatant is then transferred from the tube and subjected to a quantitative PCR test for the detection of HBV, HCV and HIV viruses in the cytoplasm of the lymphocytes, where a positive PCR for HBV indicates the presence of HBV in the donor blood.

In a standard PCR test, the detection rate of HBV and HCV has been observed at about 2.7%. According to epidemiological data, new cases of hepatitis B (HBV) and hepatitis C (HCV) transfer occur due to the transfusion of infected blood or its components in about 2.2%-5.6% of occurrences. To uncover the reasons behind this and techniques for the elimination of HBV infection in recipients, the lymphotropic properties of the virus were used.

In particular, serums from 309 donor blood samples were tested by PCR for HBV markers detection rate.

PCR revealed HBV in 6 out of 209 serum samples that estimated at about 1.94% of all number of donors' sample. The same PCR study (study of lymphocytes content from the same donors) revealed HBV in 17 out of 309 samples, estimated at about 7.44% of all donors' samples. Thus, the standard PCR testing of blood serum was false-negative in 5.50% of samples, which indicates that this is the reason for HBV infection in recipients by transfusion of infected blood or the components thereof.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

What is claimed is:

1. A method for the detection of viruses with lymphotropism properties in a biological material with a low virus concentration, comprising:
    forming an admixture of an equal amount of a biological material from a patient with a lymphocyte suspension from a healthy human subject;
    incubating the admixture;
    washing-out the lymphocytes in the admixture;
    removing lymphocyte membranes from the admixture, separating the lymphocyte cytoplasm content, thereby concentrating the lymphocyte cytoplasm content; and
    detecting the presence or absence of the virus RNA or DNA in the lymphocyte cytoplasm content,
    wherein the presence of the virus RNA or DNA in the lymphocyte cytoplasm content, with the earlier non-detection of infection, indicates the preserved viability of viruses in said biological sample of said patient,
    wherein the absence of the virus RNA or in the lymphocyte cytoplasm content indicates the loss of virus viability in said biological sample of said patient, and
    wherein said low virus concentration is below enzyme immunoassay (EIA) and polymerase chain reaction (PCR) testing sensitivity thresholds.

2. The method according to claim 1, wherein said biological materials are selected from the group consisting of plasma, blood serum, biopsy tissues or organs, medical instrument washouts, and combinations thereof.

3. The method according to claim 1, wherein the viruses detected are selected from the group consisting of HBV, HCV, HIV, and combinations thereof.

4. The method according to claim 1, wherein said admixture is incubated at about 37° C. for about 6-8 hours.

5. The method according to claim 1, wherein the detecting of the virus RNA or DNA in the lymphocyte cytoplasm content is done by polymerase chain reaction (PCR).

6. The method according to claim 1, wherein, in said step of forming, said lymphocyte suspension is from a blood sample of said healthy human subject.

7. The method according to claim 1, wherein, prior to said step of incubating, the admixture is stirred.

8. The method according to claim 1, wherein, in said step of removing lymphocyte membranes, the lymphocyte membranes are separated by centrifugation.

9. The method according to claim 1, wherein the viability of said virus RNA or DNA is the ability of the virus RNA or DNA to penetrate and persist intracellularly in the lymphocytes of at least one healthy human subject during in vitro incubation.

10. The method according to claim 1, wherein, in said step of removing, lymphocytes within said admixture are destroyed.

11. The method according to claim 10, wherein the lymphocytes are destroyed by freezing.

12. The method according to claim 1, wherein, in said step of washing-out, the lymphocytes are washed out from the plasma portion in the admixture.

13. A method for the detection of viruses with lymphotropism properties in a biological material with a low virus concentration, comprising:
   collecting a biological material from a patient;
   obtaining a lymphocyte suspension from a blood sample of at least one healthy human subject;
   forming an admixture of an equal amount of said biological material with said lymphocyte suspension;
   stirring and incubating the admixture;
   washing-out the lymphocytes from the admixture;
   removing lymphocyte membranes from the admixture, separating the lymphocyte cytoplasm content by centrifugation, thereby concentrating lymphocyte cytoplasm content; and
   detecting the presence or absence of the virus RNA or DNA in the lymphocyte cytoplasm content,
   wherein the presence of the virus RNA or DNA in the lymphocyte cytoplasm content, with the earlier non-detection of infection, indicates the preserved viability of viruses in said biological sample of said patient,
   wherein the absence of the virus RNA or in the lymphocyte cytoplasm content indicates the loss of virus viability in said biological sample of said patient, and
   wherein said low virus concentration is below enzyme immunoassay (EIA) and polymerase chain reaction (PCR) testing sensitivity thresholds.

14. The method according to claim 13, wherein, in said step of washing-out, the lymphocytes are washed out from the plasma portion in the admixture.

15. The method according to claim 13, wherein said biological materials are selected from the group consisting of plasma, blood serum, biopsy tissues or organs, medical instrument washouts, and combinations thereof.

16. The method according to claim 13, wherein the viruses detected are selected from the group consisting of HBV, HCV, HIV, and combinations thereof.

17. The method according to claim 13, further comprising, after the step of forming said admixture, the step of:
   incubating said admixture at about 37° C. for about 6-8 hours.

18. The method according to claim 17, wherein, prior to said step of incubating, the admixture is stirred.

19. The method according to claim 13, wherein the detecting of the virus RNA or DNA in the lymphocyte cytoplasm content is done by polymerase chain reaction (PCR).

20. The method according to claim 1, wherein, in said step of forming, said lymphocyte suspension is from a blood sample of said at least one healthy human subject.

* * * * *